US010045770B2

(12) United States Patent
Burkhart et al.

(10) Patent No.: US 10,045,770 B2
(45) Date of Patent: *Aug. 14, 2018

(54) METHOD FOR KNOTLESS FIXATION OF TISSUE WITH SWIVEL ANCHOR

(75) Inventors: Stephen S. Burkhart, San Antonio, TX (US); Peter J. Dreyfuss, Naples, FL (US); John A. Sodeika, Naples, FL (US); Reinhold Schmieding, Naples, FL (US)

(73) Assignee: Arthrex, Inc., Naples, FL (US)

( * ) Notice: Subject to any disclaimer, the term of this patent is extended or adjusted under 35 U.S.C. 154(b) by 45 days.

This patent is subject to a terminal disclaimer.

(21) Appl. No.: 13/412,163

(22) Filed: Mar. 5, 2012

(65) Prior Publication Data

US 2012/0165868 A1 Jun. 28, 2012

Related U.S. Application Data

(63) Continuation of application No. 12/368,946, filed on Feb. 10, 2009, now abandoned, which is a
(Continued)

(51) Int. Cl.
*A61B 17/04* (2006.01)
*A61B 17/00* (2006.01)
*A61B 17/86* (2006.01)

(52) U.S. Cl.
CPC .............. *A61B 17/0401* (2013.01);
*A61B 2017/00893* (2013.01); *A61B 2017/044* (2013.01);
(Continued)

(58) Field of Classification Search
CPC ........ A61B 17/0401; A61B 2017/0409; A61B 2017/0401; A61B 2017/044; A61B 2017/0445; A61B 2017/045; A61B 2017/8655; A61B 2017/0446; A61B 2017/0448; A61B 2017/0414;
(Continued)

(56) References Cited

U.S. PATENT DOCUMENTS 3,762,418 A * 10/1973 Wasson ............ A61B 17/06004
606/226
4,484,570 A 11/1984 Sutter et al.
(Continued)

FOREIGN PATENT DOCUMENTS

| EP | 1 857 054 A2 | 11/2007 |
| WO | WO 2006/060035 A2 | 6/2006 |
| WO | WO 2006/099109 A2 | 9/2006 |

*Primary Examiner* — Christopher L Templeton
(74) *Attorney, Agent, or Firm* — Blank Rome LLP (57) ABSTRACT

A fenestrated suture anchor for fixation of tissue to bone. In a preferred embodiment, the suture includes an implant, such a swivel implant with a forked tip for capturing suture. The implant is secured in a hole in bone by advancing a fixation device, such as a cannulated interference screw, to engage and fully seat the implant. The cannulated fixation device is provided with a plurality of openings or fenestrations of various dimensions and geometries to provide multiple pathways through the anchor (i.e., though the interior of the body and through the fenestrations) to allow blood to flow to increase the healing zone, for example, for rotator cuff repair, while also promoting bone in-growth.

2 Claims, 12 Drawing Sheets

Related U.S. Application Data continuation-in-part of application No. 12/043,008, filed on Mar. 5, 2008, now abandoned, which is a continuation-in-part of application No. 11/802,057, filed on May 18, 2007, now Pat. No. 9,005,246, application No. 12/368,946, filed on Feb. 10, 2009, which is a continuation-in-part of application No. 11/392,798, filed on Mar. 30, 2006, now Pat. No. 7,803,173.

(60) Provisional application No. 60/801,097, filed on May 18, 2006, provisional application No. 60/666,518, filed on Mar. 30, 2005.

(52) U.S. Cl.
CPC . *A61B 2017/045* (2013.01); *A61B 2017/0408* (2013.01); *A61B 2017/0409* (2013.01); *A61B 2017/0412* (2013.01); *A61B 2017/0438* (2013.01); *A61B 2017/8655* (2013.01)

(58) Field of Classification Search
CPC .... A61B 2017/0458; A61B 2017/0422; A61B 2017/0424; A61B 2017/0425; A61B 2017/0429; A61B 2017/043; A61B 2017/0432; A61B 2017/0433; A61B 2017/0435; A61B 2017/0437; A61B 2017/0438
USPC .......................................................... 606/232
See application file for complete search history.

(56) References Cited

U.S. PATENT DOCUMENTS

| | | | |
|---|---|---|---|
| 4,870,957 A * | 10/1989 | Goble | A61B 17/686 606/309 |
| 5,084,050 A | 1/1992 | Draenert | |
| 5,129,904 A | 7/1992 | Illi | |
| 5,152,790 A * | 10/1992 | Rosenberg | A61F 2/0811 606/304 |
| 5,249,899 A | 10/1993 | Wilson | |
| 5,368,595 A * | 11/1994 | Lewis | A61B 17/0401 606/151 |
| 5,500,000 A * | 3/1996 | Feagin et al. | 606/232 |
| 5,702,398 A * | 12/1997 | Tarabishy | A61F 2/0811 606/104 |
| 5,860,973 A | 1/1999 | Michelson | |
| 5,968,047 A | 10/1999 | Reed | |
| 6,045,574 A * | 4/2000 | Thal | 606/232 |
| 6,048,343 A | 4/2000 | Mathis et al. | |
| 6,143,017 A | 11/2000 | Thal | |
| 6,355,043 B1 | 3/2002 | Adam | |
| 6,517,542 B1 | 2/2003 | Papay et al. | |
| 6,544,281 B2 | 4/2003 | ElAttrache et al. | |
| 6,589,245 B1 | 7/2003 | Weiler et al. | |
| 6,863,671 B1 | 3/2005 | Strobel et al. | |
| 6,939,135 B2 | 9/2005 | Sapian | |
| 7,083,647 B1 | 8/2006 | Sklar et al. | |
| 7,261,716 B2 | 8/2007 | Strobel et al. | |
| 7,300,439 B2 | 11/2007 | May | |
| 7,329,272 B2 | 2/2008 | Burkhart et al. | |
| 7,572,283 B1 * | 8/2009 | Meridew | A61F 2/0805 606/232 |
| 7,717,947 B1 | 5/2010 | Wilberg et al. | |
| 7,976,565 B1 * | 7/2011 | Meridew | A61B 17/0401 606/1 |
| 7,981,140 B2 * | 7/2011 | Burkhart | 606/232 |
| 8,012,174 B2 * | 9/2011 | ElAttrache et al. | 606/232 |
| 2002/0013608 A1 | 1/2002 | ElAttrache et al. | |
| 2002/0156476 A1 * | 10/2002 | Wilford | A61F 2/0805 606/232 |
| 2003/0153947 A1 * | 8/2003 | Koseki | 606/228 |
| 2004/0093030 A1 * | 5/2004 | Cox | A61B 17/0401 606/232 |
| 2004/0093031 A1 | 5/2004 | Burkhart et al. | |
| 2004/0193217 A1 | 9/2004 | Lubbers et al. | |
| 2004/0225292 A1 | 11/2004 | Sasso et al. | |
| 2006/0004364 A1 | 1/2006 | Green et al. | |
| 2006/0079904 A1 * | 4/2006 | Thal | 606/72 |
| 2006/0247642 A1 | 11/2006 | Stone et al. | |
| 2006/0259076 A1 | 11/2006 | Burkhart et al. | |
| 2007/0060922 A1 | 3/2007 | Dreyfuss | |
| 2007/0135843 A1 * | 6/2007 | Burkhart | 606/232 |
| 2007/0167958 A1 * | 7/2007 | Sulamanidze | A61B 17/06166 606/139 |
| 2007/0191849 A1 | 8/2007 | ElAttrache et al. | |
| 2007/0225719 A1 * | 9/2007 | Stone et al. | 606/72 |
| 2008/0004659 A1 | 1/2008 | Burkhart et al. | |
| 2008/0154314 A1 | 6/2008 | McDevitt | |
| 2008/0208253 A1 | 8/2008 | Dreyfuss et al. | |
| 2008/0215091 A1 | 9/2008 | Dreyfuss et al. | |
| 2008/0275431 A1 * | 11/2008 | Stone et al. | 606/1 |
| 2008/0281325 A1 | 11/2008 | Stone et al. | |
| 2009/0187216 A1 | 7/2009 | Schmieding et al. | |
| 2009/0192546 A1 | 7/2009 | Schmieding et al. | |
| 2011/0313455 A1 * | 12/2011 | ElAttrache et al. | 606/232 |
| 2013/0035721 A1 * | 2/2013 | Brunelle | 606/232 |

\* cited by examiner

METHOD FOR KNOTLESS FIXATION OF TISSUE WITH SWIVEL ANCHOR

CROSS-REFERENCE TO RELATED APPLICATIONS

This is a continuation of U.S. application Ser. No. 12/368,946, filed on Feb. 10, 2009, now abandoned, which is a continuation-in-part of U.S. application Ser. No. 12/043,008, filed on Mar. 5, 2008, now abandoned, which in turn is a continuation-in-part of U.S. application Ser. No. 11/802,057, filed on May 18, 2007, now U.S. Pat. No. 9,005,246 which claims the benefit of U.S. Provisional Application Ser. No. 60/801,097, filed on May 18, 2006, the entire disclosures of which are incorporated by reference herein. This application is also a continuation-in-part application of U.S. application Ser. No. 11/392,798, filed on Mar. 30, 2006, now U.S. Pat. No. 7,803,173, which claims the benefit of U.S. Provisional Application Ser. No. 60/666,518, filed on Mar. 30, 2005, the entire disclosures of which are also incorporated by reference herein.

FIELD OF THE INVENTION

The present invention relates to surgical fixation and, more particularly, to methods of conducting anatomical tissue repair, such as ligament repair and reconstruction, using a fenestrated suture anchor.

BACKGROUND OF THE INVENTION

Securing suture during surgery can be difficult and demanding. Various suture constructs have been developed in an effort to avoid the need to tie knots in suture, particularly during arthroscopic surgery. For example, U.S. Pat. No. 6,143,017 to Thal discloses tissue fixation using a free-standing continuous suture loop that is snagged by an anchoring device. While it appears that tissue can be bound to bone according to the Thal teachings, it is not evident how to accomplish in situ surgical refinements such as adjustment of the loop length or tension on the repaired tissue. Accordingly, there exists a need in the art for improved technology for knotless tissue fixation. A need also exists for a knotless suture anchor with fenestrated configuration that promotes healing of tissue.

SUMMARY OF THE INVENTION

The present invention provides apparatus and methods for anatomical tissue repair and reconstruction, using a fenestrated suture anchor for knotless tissue fixation. In one method of tissue fixation, a swivel implant is used to capture a suture chain formed of at least two loops formed of high strength suture. A driver is provided direct the tip of the swivel implant to capture loops of the suture chain. The swivel implant is locked and secured in bone by inserting a cannulated fixation device (for example, an interference plug or screw) over the implant. The cannulated fixation device is provided with a plurality of openings or fenestrations of various dimensions and geometries to provide multiple pathways through the device (i.e., though the interior of the body and through the fenestrations) to allow blood to flow to increase the healing zone, for example, for rotator cuff repair, while also promoting bone in-growth.

Other features and advantages of the present invention will become apparent from the following description of exemplary embodiments of the invention described with reference to the accompanying drawings.

BRIEF DESCRIPTION OF THE DRAWINGS

FIGS. 17(*a*) and 17(*b*) illustrate various views of a driver assembly comprising a rod, an inserter member, a threaded gauge and an end piece, according to the present invention.

DETAILED DESCRIPTION OF THE INVENTION

The present invention provides apparatus and methods for knotless tissue fixation using a swivel suture anchor. In a preferred method, the swivel suture anchor is used with a suture chain formed of at least two loops of suture, preferably high strength suture. The loops of the chain are captured by mounting the swivel implant on a driver. The driver is also used to engage and lock the swivel implant in a hole in bone by inserting a cannulated fixation device (for example, an interference plug or screw) over the anchor.

The present invention also provides a method for knotless fixation of anatomical tissue during surgical applications by employing a swivel suture anchor. Suture chains used in accordance with the present invention are described in detail in U.S. Application Publication No. 2006/0259076, the entire disclosure of which is incorporated by reference herein. The term "chain" is used in the specification and claims to refer to exemplary embodiments of the invention. A "chain" in this context refers broadly to a suture construct formed of a series of suture loops. The loops can be, but need not be, interlinked. In this manner, the term "chain" as used in this application includes, but need not be limited to, the commonly understood definition in which links or rings are fitted into one another. Rather, the chains of the present invention can include two or more loops that are connected together. Each loop preferably has a fixed perimeter. The suture can be interlaced, rather than knotted, as described further below, to establish and maintain loop geometry. Preferably, all loops are similar in size.

Referring now to the drawings, where like elements are designated by like reference numerals, FIGS. 1-16 illustrate two surgical procedures of approximating tissue (for example, a torn tendon) to bone according to exemplary embodiments of the present invention. For simplicity, the invention will be described below with reference to fixation of the rotator cuff; however, the invention is not limited to this exemplary embodiment and has applicability to fixation of tissue in general, such as, for example, fixation of torn tendons in ACL reconstructions of the knee or in fixation of any tendon to bone.

Method steps of tissue fixation according to exemplary embodiments of the present invention are depicted schematically in FIGS. 1-16. As described in more detail below, FIGS. 1-8 illustrate sequential steps during a rotator cuff repair using a knotless single row technique and FIGS. 9-16 illustrate sequential steps during a rotator cuff repair using a knotless double row technique. Both techniques will be described with reference to driver assembly 100 (FIGS. 17-20), swivel lock anchor 200 (FIG. 21) and fixation device 300 (FIG. 22).

Although the single and double row techniques are described below with reference to specific instruments sold by Arthrex, Inc., the assignee of the present application, and with reference to a series of specific steps and devices used during the surgical tissue fixation, it should be understood that the invention is not limited to the specific disclosure of these embodiments and contemplates modifications and variations that are apparent to those skilled in the art. Accordingly, the invention must not be limited to the specific embodiments detailed below, as they are only exemplary in nature.

Knotless Single Row Repair Technique—FIGS. 1-8

FIGS. 1-8 illustrate a series of subsequent steps in shoulder repair for a single-row repair technique using a swivel suture anchor according to the present invention.

Figure 1:
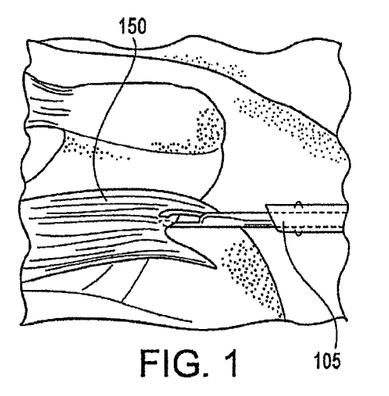
FIGS. 1-8 depict a series of subsequent steps of shoulder repair using a single-row technique with a swivel suture anchor according to the present invention.

The mobility of the tear is assessed using a suture retriever/tissue grasper 105, such as the Arthrex King-Fisher™ Suture Retriever/Tissue Grasper, as shown in FIG. 1. In the case of a large U-shaped tear, margin convergence suturing may be required before approximation. Then, a shaver, high-speed burr, or chondro pick is used to prepare a bleeding bone bed.

Figure 2:
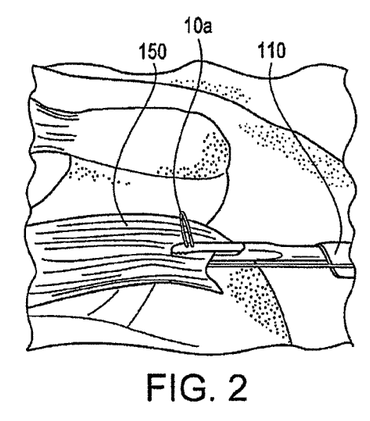

As shown in FIG. 2, the non-linked, free end 10*a* of a suture chain 10, such as the Arthrex FiberChain, is passed through the rotator cuff 150 using a suture passer 110, such as the Arthrex Scorpion™ Suture Passer, through a cannula, such as an Arthrex 5.75 mm Crystal Cannula. Next, the suture is retrieved through the same cannula.

Figure 3:
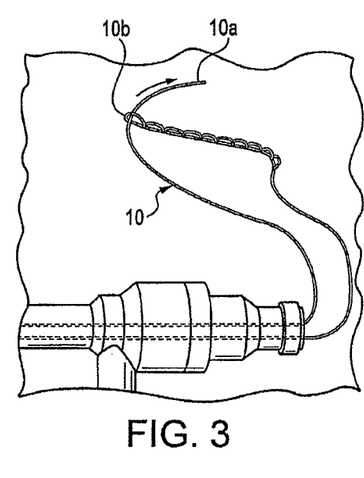

Then the free end 10*a* of suture chain 10 is passed through the terminal link 10*b* at its opposite end, as shown in FIG. 3. The loop 10*b* is cinched down by pulling on the free end 10*a* of the suture chain 10. The tip of the cannula may be used to help seat the suture chain loop securely against the rotator cuff 150. A suture retriever/tissue grasper 105 may be useful to ensure that the loop has been fully tightened. The second suture chain 11 is passed through the rotator cuff 150, the free end passed through the terminal loop, and the loop cinched in the same manner as for the first suture chain 10.

Figure 4:
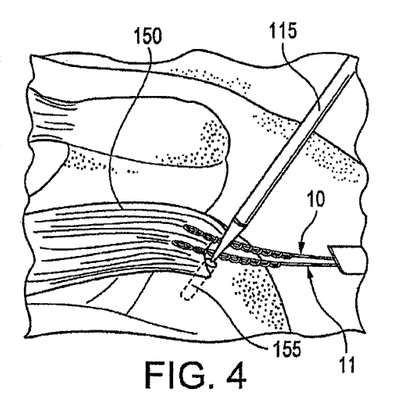

As shown in FIG. 4, the suture chain 10, 11 is used as a traction suture to determine the desired anchor location adjacent to the rotator cuff margin and a bone socket 155 is punched through a superolateral percutaneous portal with a punch 115, such as the Arthrex 5.5 mm Bio-Corkscrew FT Punch. A second bone socket 155 is also formed in the same manner for the second fiber chain 11.

Figure 5:
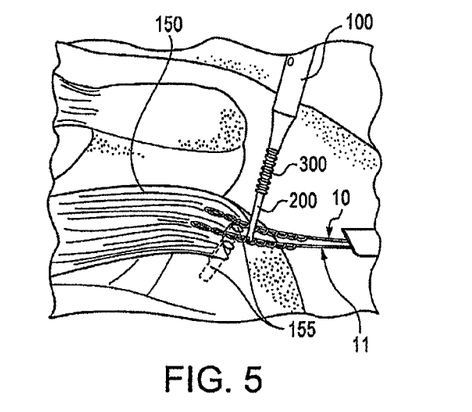

As shown in FIG. 5, both suture chain ends 10*a*, 11*a* are retrieved through the lateral portal. The swivel implant 200 of the present invention is introduced through the percutaneous superolateral portal and captures the third link 10*c* from the free margin of the rotator cuff 150. The link 10*c* is captured by the forked anchor tip 250 of the anchor 200 (see FIG. 21). In a preferred embodiment, each link in the suture chain 10 is approximately 6 mm in length; therefore, since the total length of the swivel implant 200 is 18 mm, capturing the third link 10*c* from the cuff edge will usually position the cuff directly at the edge of the bone socket 155 and perfectly tension the suture chain 10 and the rotator cuff 150 segment that it spans, when the anchor tip 250 pushes the suture chain 10 to the bottom of the bone socket 155.

Figure 6:
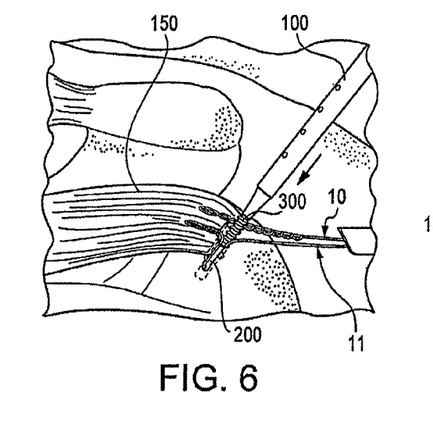
Figure 6A:
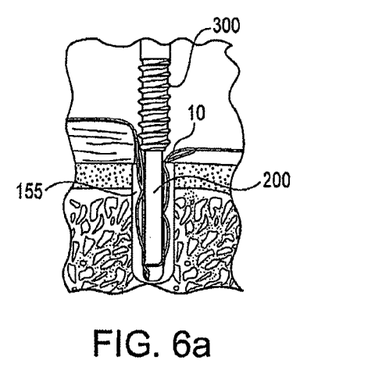

The tissue tension is then evaluated, as shown in FIG. 6. The driver assembly 100 is advanced into the bone socket 155 and the suture chain 10 is pushed toward the bottom of the socket 155 until the anchor body 225 contacts the bone. If the tension is not adequate, the driver 100 is removed from the bone socket 155 by pulling on the free end of the suture chain 10 (to release any wedging of the swivel-tip 250) at the same time that the driver assembly 100 is withdrawn. Then the adjacent, more proximal link is instead captured. If the tension is too great to fully insert the driver 100 to the bottom of the bone socket 155, the driver 100 is removed and the adjacent, more distal link is captured. Then the driver 100 is reinserted to the base of the bone socket. The forked tip 250 of the swivel implant 200 is held to the driver with a zero retention suture cleated at the driver's proximal end.

Figure 7:
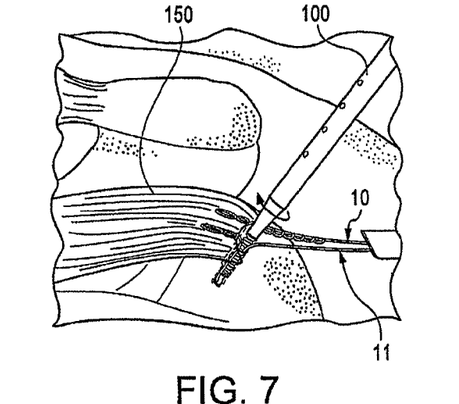
Figure 7A:
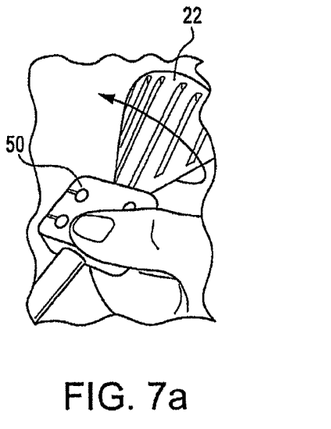

Fixation device 300, such as a screw, is advanced by driver assembly 100 by holding the thumb pad 50 as the inserter handle 22 is turned clockwise, as shown in FIG. 7(*a*). When the swivel anchor construct 400 is fully seated, the shaft 225 of the swivel implant 200 is fully engaged by the fixation device 300 to optimize the stability of the swivel implant construct 400. The swivel anchor construct 400 comprises swivel implant 200 and fixation device 300. The tip retention suture is unwound from the cleat at the back of the driver handle 22 and the driver assembly 100 is removed. Then, one limb of the retention suture is pulled to fully remove it from the implant.

Figure 8:
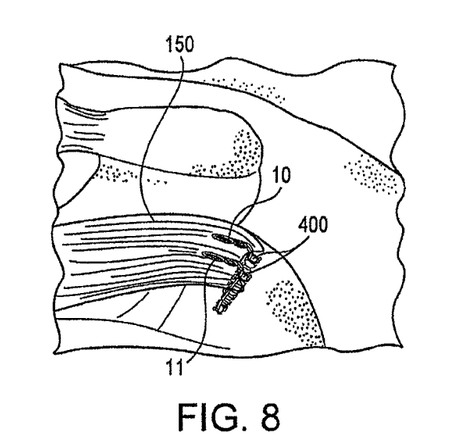
Figure 8A:
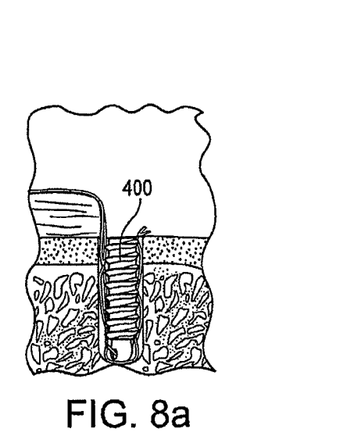

The insertion steps are repeated for the second swivel anchor construct 400 to obtain the final suture/anchor construct, shown in FIG. 8. The free suture ends 10*a*, 11*a* are cut with a suture cutter, such as the Arthrex open ended Fiber-Wire Suture Cutter, so that they are flush with the edge of the bone socket 155.

Knotless Double Row Repair Technique—FIGS. 9-16

FIGS. 9-16 illustrate a series of subsequent steps in shoulder repair for a double-row repair technique using a swivel suture anchor according to the present invention.

Figure 9:
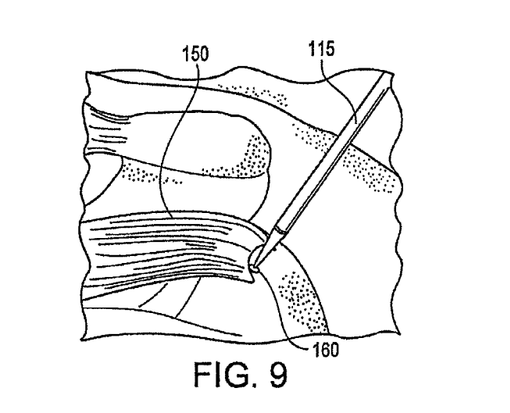
FIGS. 9-16 depict a series of subsequent steps of shoulder repair using a double-row technique with a swivel suture anchor according to the present invention.

The mobility of the tear is assessed using suture retriever/tissue grasper. In the case of a large U-shaped tear, margin convergence suturing may be required before approximation of the tendon. A shaver, high-speed burr, or chondro pick is used to prepare a bleeding bone bed. Then, as shown in FIG. 9, pilot holes 160 are prepared for two suture anchors 120, such as Arthrex Bio-Corkscrew FT suture anchors, that will comprise the medial row through a percutaneous superolateral portal. A punch 115, such as the Arthrex 5.5 mm Bio-Corkscrew FT Punch, is advanced to the laser line at a 45° "deadman" angle, adjacent to the articular margin of the humerus to form the pilot holes 160. Tapping is seldom, but may be, necessary.

Figure 10:
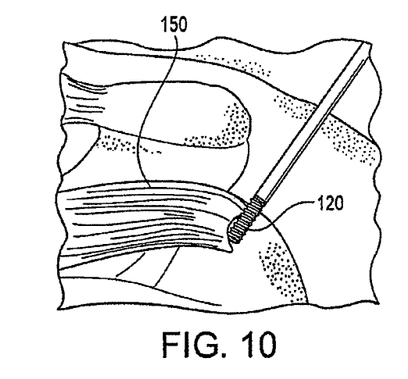
Figure 10A:
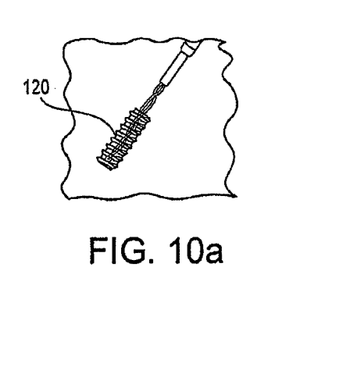

As shown in FIG. 10, both suture anchors 120 are placed. In a preferred embodiment, the suture anchors 120 come preloaded with suture chain 10.

Figure 11:
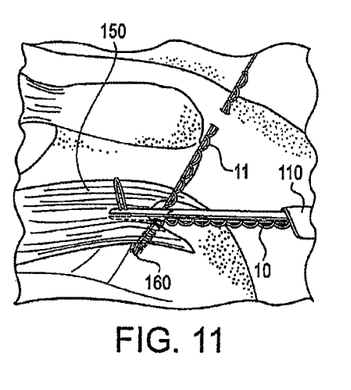

Then, as shown in FIG. 11, the suture leader is retrieved from one of the suture chain 10 strands through the lateral portal and is loaded onto a suture passer 110, such as the Arthrex Scorpion Suture Passer. The suture chain 10 is passed through the rotator cuff 150 approximately 15 mm from the free margin of the rotator cuff 150. This step is then repeated for the second suture chain 11.

Figure 12:
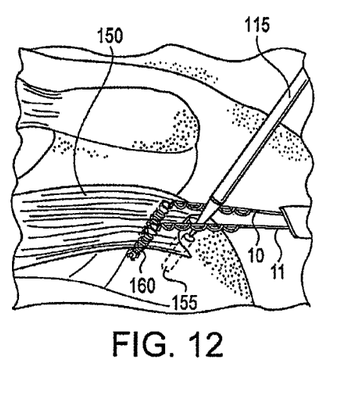

As shown in FIG. 12, both suture chain suture ends 10a, 11a are retrieved through the lateral portal and are tensioned to bring the cuff into contact with the medial portion of the footprint. The tip of the cannula may be used to push the tendon against the footprint. Then two bone sockets 155 are formed for the lateral row swivel implants 200 using a punch 115. These two bone sockets 155 should be adjacent to the lateral margin of the cuff 150 when the cuff 150 is appropriately tensioned by the two previously placed suture chains 10, 11.

Figure 13:
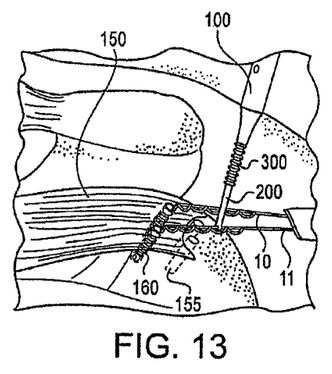

As shown in FIG. 13, the swivel implant 200 is introduced through the percutaneous superolateral portal, capturing the third link 10c from the free margin of the rotator cuff 150. The link 10c is captured by the forked anchor tip 250 of the swivel implant 200 (see FIG. 21). In a preferred embodiment, each link in the suture chain 10, 11 is approximately 6 mm in length; therefore, since the total length of the swivel implant 200 is 18 mm, capturing the third link from the cuff edge will usually position the cuff directly at the edge of the bone socket 155 and perfectly tension the suture chain 10 and the rotator cuff segment that it spans when the anchor tip 250 pushes the suture chain 10 to the bottom of the bone socket 155.

Figure 14:
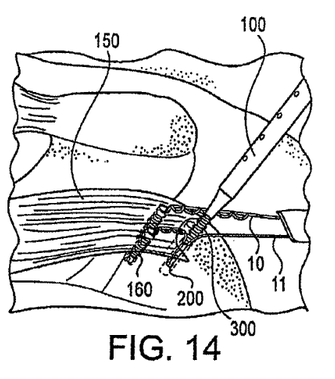

The tissue tension is then evaluated, as shown in FIG. 14. The driver assembly 100 is advanced into the bone socket 155 and the suture chain 10 is pushed toward the bottom of the socket 155 until the anchor body 225 contacts the bone. If the tension is not adequate, the driver is removed from the bone socket by pulling on the free end of the suture chain 10 (to release any wedging of the swivel-tip 250) at the same time that the driver assembly 100 is withdrawn and the adjacent, more proximal link is instead captured. If the tension is too great to fully insert the driver to the bottom of the bone socket 155, the driver assembly 100 is removed and the adjacent, more distal link is instead captured. Then the driver 100 is reinserted to the base of the bone socket 155.

Figure 15:
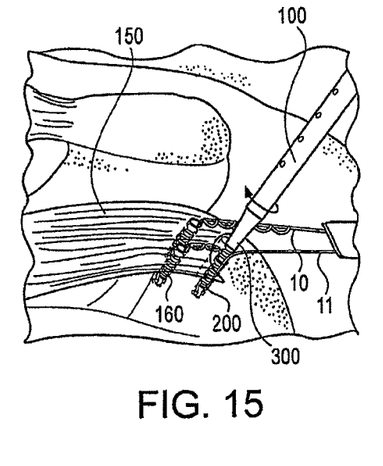
Figure 15A:
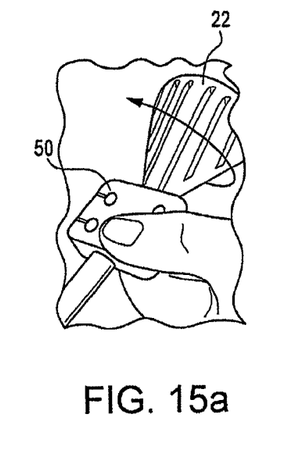

Fixation device 300, e.g., a screw, is advanced by holding the thumb pad 50 as the inserter handle 22 is turned clockwise, as shown in FIG. 15. When the swivel anchor 400 is fully seated, the shaft 225 of the swivel implant 200 is fully engaged by the body of the fixation device 300 to optimize the stability of the swivel implant construct 400. As previously stated, the swivel anchor construct 400 comprises anchor 200 and fixation device 300. The tip retention suture is unwound from the cleat at the back of the driver handle 200 and the driver 100 is removed. One limb of the retention suture is pulled to fully remove it from the implant.

Figure 16:
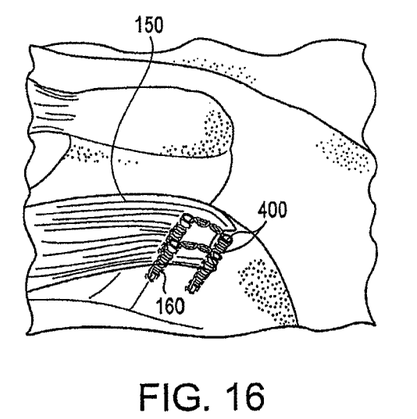
Figure 16A:
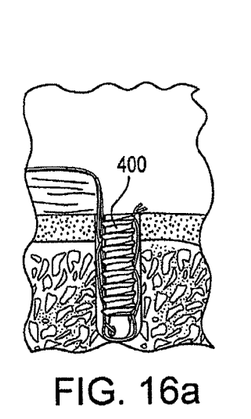

The steps of FIGS. 13-15 are then repeated for the second swivel implant construct 400 to obtain the final construct, shown in FIG. 16. The free suture ends are cut with a suture cutter so that they are flush with the edge of the bone socket 155.

In addition to the above exemplary embodiments, the invention may also be used for a side-to-side closure of soft tissue using a suture chain 10. This method includes using the suture chain 10 to perform the side-to-side closure of the soft tissue with a final step of anchoring a chain link at the lateral aspect of the repair to bone using an anchor, such as anchor 200. The anchoring step is the same as that illustrated in the first two embodiments. Furthermore, if the soft tissue split to be repaired overlies bone for its entire length, a suture anchor, similar to suture anchor 120, may be inserted into bone at the medial aspect of the repair, a side-by-side margin convergence is implemented using the suture chain in a "shoelace-type" stitch, and the suture chain is anchored at the lateral aspect of the repair to bone using an anchor, such as anchor 200.

Figure 17A:
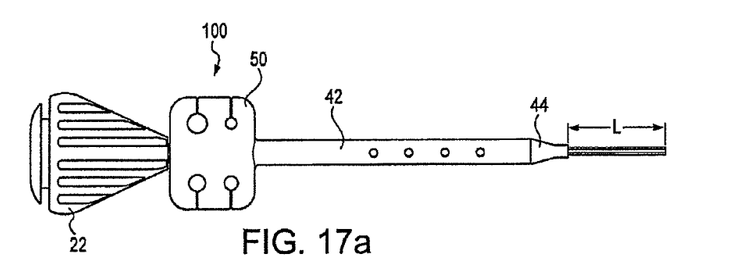
Figure 17B:
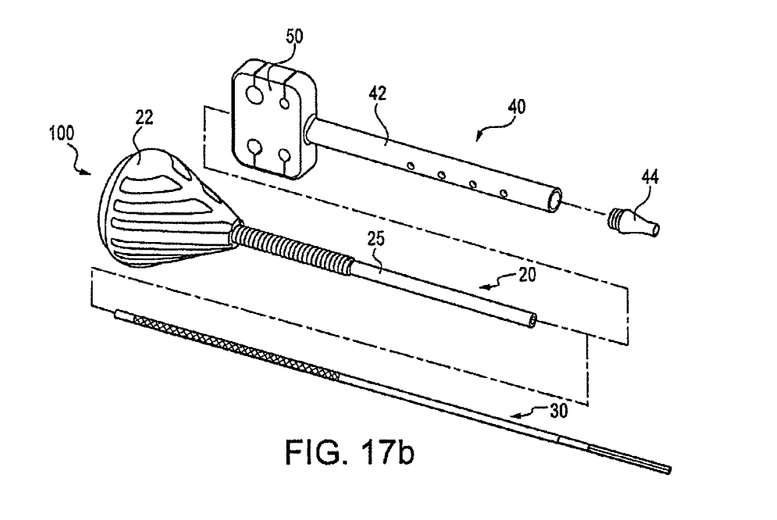
Figure 18:
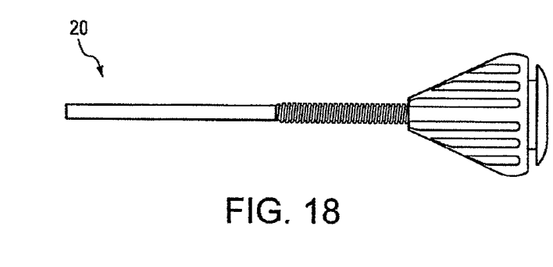
FIG. 18 illustrates various views of the inserter member of the driver assembly of FIG. 17(*a*).
Figure 19:
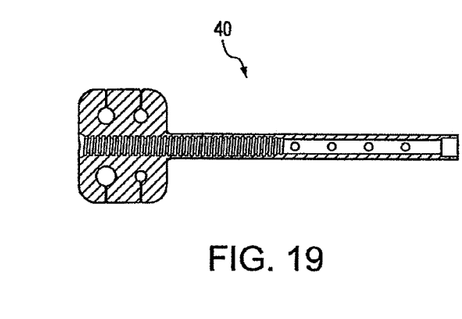
FIG. 19 illustrates various views of the threaded gauge with thumb pad of the driver assembly of FIG. 17(*a*).
Figure 20:
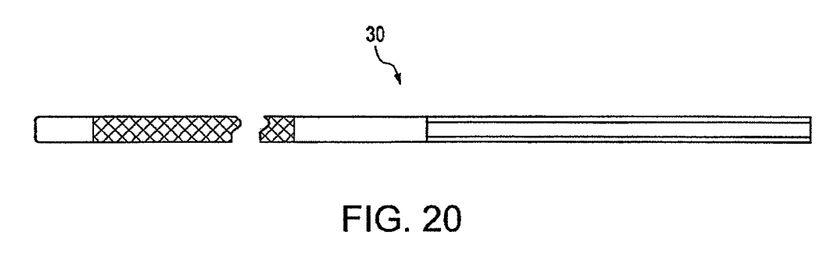
FIG. 20 illustrates various views of the rod of the driver assembly of FIG. 17(*a*).

Reference is now made to FIGS. 17(a)-22, which illustrate details of the driver assembly 100 (FIGS. 17(a)-20), the swivel implant 200 (FIG. 21) and the fixation device 300 (FIG. 22). As illustrated in FIGS. 17(a)-20, driver assembly 100 comprises a cannulated driver 20 including shaft 25 and inserter handle 22; tube or rod 30 that passes slidably and rotatably through the cannulated driver 20; threaded gauge 40 including a cannulated body 42 and thumb pad 50; and tip 44. FIGS. 17(a) and (b) illustrate the driver assembly 100 both in assembled (A) (FIG. 17(a)) and unassembled (B) (FIG. 17(b)) form. FIG. 18 provides a more detailed view of the cannulated driver 20 of the driver assembly 100. FIG. 19 provides a more detailed view of the threaded gauge 40 of the driver assembly 100. FIG. 20 provides a more detailed view of the rod 30 of the driver assembly 100.

Figure 21:
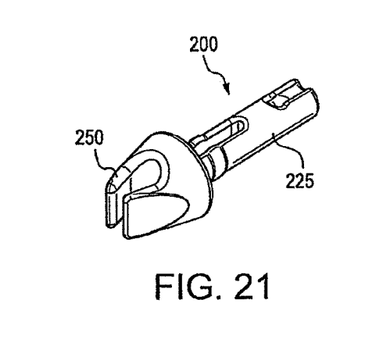
FIG. 21 illustrates various views of a swivel implant according to the present invention.
Figure 22:
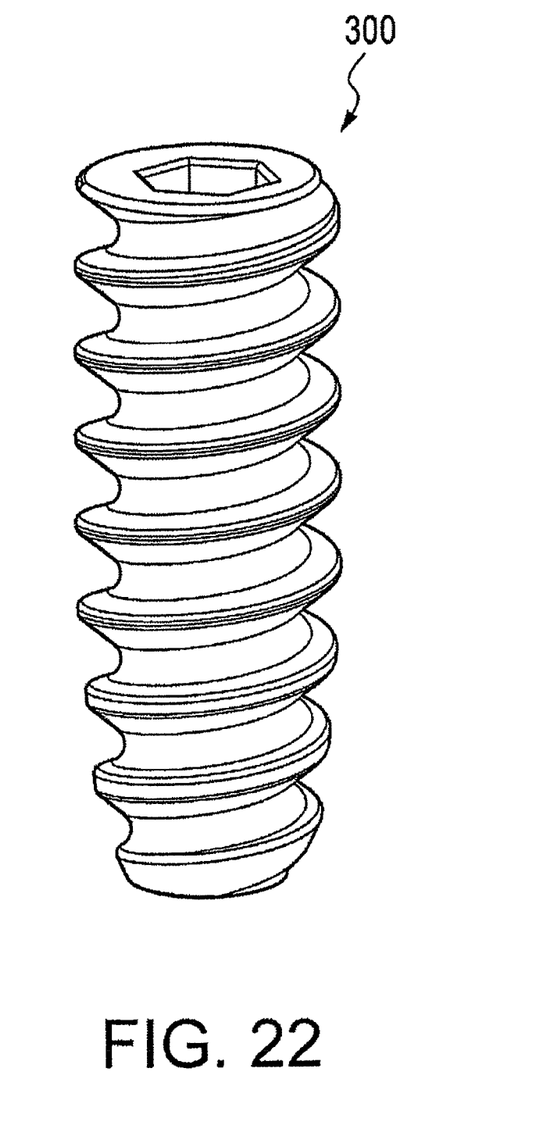
FIG. 22 illustrates various views of a fixation device according to a first embodiment of the present invention and used in conjunction with the swivel implant of FIG. 20 and the driver of FIG. 17(*a*).
Figure 23:
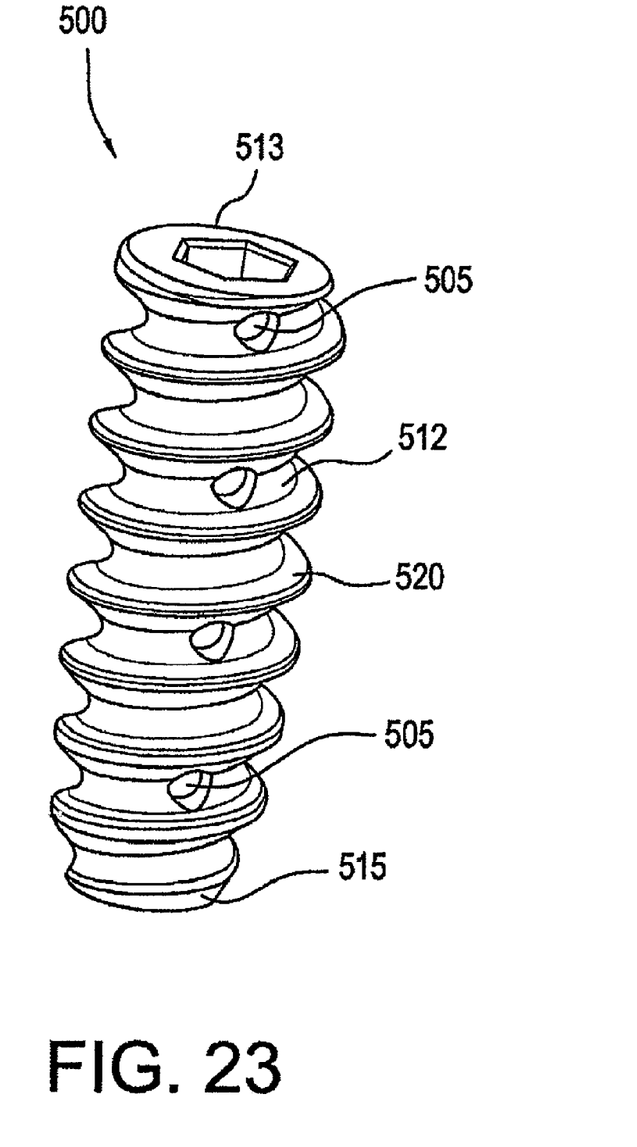
FIGS. 23-26 illustrate various views of a fixation device with fenestrations according to a second embodiment of the present invention and used in conjunction with the swivel implant of FIG. 20 and the driver of FIG. 17(*a*).
Figure 24:
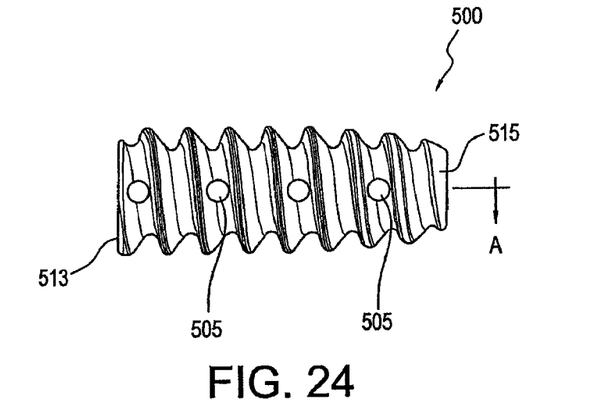

FIG. 21 illustrates various views of swivel implant 200. During installation of swivel implant 200, the implant body 225 is assembled onto the operational end of the driver 100. The implant tip 250 is threaded or otherwise attached onto the tip of thin rod or tube 30. As detailed above, forked tip 250 is used to capture a suture chain 10, 11 (that has been laced through a shoulder ligament, as shown in the two exemplary embodiments above) for installation into a pre-drilled hole 155 in bone. The implant 200 has a threaded body 225 and a detachable forked tip 250. The forked tip 250 may be rotatably attached to the implant body 225. This enables rotational insertion of the implant 200 without causing excessive twisting and knotting of the suture chain 10, 11 by the forked tip 250.

FIG. 22 illustrates various views of a fixation device 300 (for example, a cannulated interference screw) that is employed in conjunction with the driver assembly 100 and the swivel implant 200. Preferably, the fixation device 300 is preloaded on the driver assembly 100. As described above with reference to the two exemplary embodiments, the fixation device 300 is advanced into the bone socket 155 by holding the thumb pad 50 as the inserter handle 22 is turned clockwise. When the fixation device 300 is fully seated, the shaft 225 of the forked swivel implant 200 is fully engaged by the fixation device 300 to optimize the stability of the swivel implant construct 400. As previously stated, the swivel implant construct 400 is composed of anchor 200 and fixation device 300.

In the two exemplary embodiments detailed above, suture anchor 400 is an Arthrex SwiveLock™ (swivel suture anchor). However, suture anchor 400 may be also a bone anchor or an Arthrex Push-Lock™-type anchor including a forked tip in order to capture a given link of the suture chain. Alternatively, the suture chain 10, 11 passed through the tissue can be secured either using a single anchor or a plurality of anchors. In addition, various anchors, such as those noted above and others, may be used interchangeably with only slight variations in the above procedure. For example, the suture chain 10, 11 can be secured by capturing two of the chain loops in forked tines prior to insertion of the anchor or anchors.

Further, regular suture may be used in addition to the suture chains of the present invention. In this case, the first suture anchor 120 of the double row embodiment will be pre-loaded with regular suture (for example, the Arthrex BioCorkscrew™ or Arthrex BioCorkscrew-FT™, disclosed in U.S. Application Publication No. 2007/0060922). In an exemplary embodiment using regular suture, the technique is similar to the one described above, except that the lateral fixation is accomplished by capturing the suture limbs (rather than chain-links) in the fork of the implant 200 and tensioning the suture as the implant 200 is placed. This relies on interference fixation of the suture between the implant 200 and the bone.

As described above, the swivel anchor and suture chain assembly of the present invention has application in surgical tissue repair, for example, in conjunction with one or more bone anchors. Tension on repair constructs is adjustable through selection of the chain link or links to be snagged by a bone anchor.

FIGS. 23-26 illustrate various views of another exemplary fixation device 500 of the present invention that is employed in conjunction with the driver assembly 100 and the swivel implant 200. The fixation device 500 is similar to the fixation device 300 of FIG. 22, but differs from it in that the fixation device 500 is provided with a plurality of openings or fenestrations 505 provided on the outer surface of the body of the device. The openings or fenestrations 505 may have various dimensions and geometries provide multiple pathways for w blood to pass through the device (i.e, through the fenestrations and up through the cannulation) and, therefore, to the repair site to promote healing. The fenestrations also promote in-growth of bone. The decreased mass of the device 500 (resulting from the fenestrations) further promotes healing and in-growth.

Preferably, the fixation device 500 is preloaded on the driver assembly 100. As described above with reference to the three exemplary embodiments, the fixation device 500 is advanced into the bone socket 155 by holding the thumb pad 50 as the inserter handle 22 is turned clockwise. When the fixation device 500 is fully seated, the shaft 225 of the forked swivel implant 200 is fully engaged by the fixation device 500 to optimize the stability of the swivel anchor construct (composed of implant 200 and fixation device 500).

Figure 25:
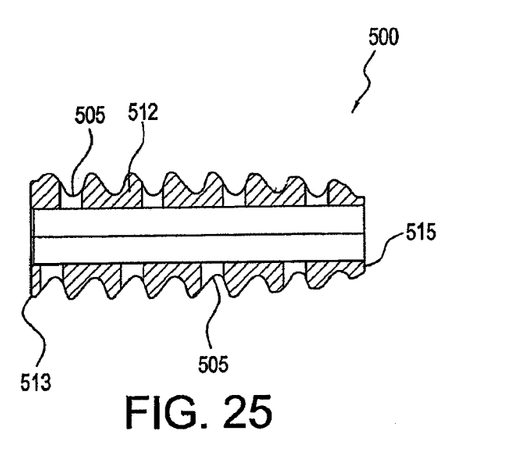
Figure 26:
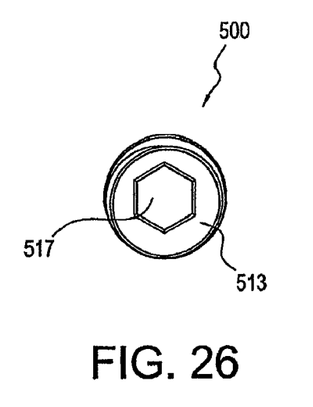

As illustrated in FIGS. 23-26, the fixation device 500 includes a cannulated body 512 in the form of a tapered cylinder having a proximal end 513 and a distal end 515. A continuous thread 520 wraps around cannulated body 512 in a clockwise direction, as shown. As shown in FIG. 25, the distal end 515 of the interference screw 500 terminates in an exposed, flat surface provided with an opening 516. The proximal end 513 of the interference screw 500 terminates in a drive socket 517 that allows a driver to seat snuggly in the drive socket to allow manipulation and installation of the interference screw into the bone socket, while fully engaging the shaft of the swivel implant 200 (as detailed above with reference to interference crew 300). As shown in FIG. 26, drive socket 517 may be configured to be used with a traditional hex drive screwdriver. Although the drive socket 517 has been described as having hexagonal shape, the drive socket may also have a Delta drive configuration or a cruciform shape, among others, that allows the driver to rotationally engage the interference screw, to turn simultaneously with the driver.

The fixation device 500 of the present invention may be formed of a biocompatible and/or biosorbable material. Preferably, screw 500 is formed of a bioabsorbable material, such as poly-(L-lactic acid) (PLLA), poly-(D,L-lactide), and poly glycolic acid (PGA), for example, or other bioabsorbable, non-metallic materials, which may be especially tailored for hardness, tensile strength and compressive strength. Alternatively, fixation device 500 may be formed of titanium, titanium alloy, stainless steel or stainless steel alloy. Other biocompatible materials which could be used include plastics, allograft bone and inert bone substitute materials.

A growth material may be advanced through the cannulated driver and into the screw 500 by employing a plunger, for example. As the driver is pulled out, the plunger pushes the flow material through the cannulation of the driver and into the body of the screw 500. The growth material will subsequently harden to allow better fixation of the interference screw 500 against the bone and the shaft of the swivel implant 200.

The growth material may be any solid, semi-solid, viscous, flowable, gel or elastic composition or mixture that allows its easy manipulation and insertion into the body 512 of the interference screw 500. The growth material may contain growth factors such as autogenous growth factors, for example platelet-rich plasma (PRP), optionally in combination with hyaluronic acid (HY acid) and/or with a coagulant such as thrombin.

The term "growth factor" as used in the present application is intended to include all factors, such as proteinaceous factors, for example, which play a role in the induction or conduction of growth of bone, ligaments, cartilage or other tissues associated with bone or joints. In particular, these growth factors include bFGF, aFGF, EGF (epidermal growth factor), PDGF (platelet-derived growth factor), IGF (insulin-like growth factor), TGF-β. I through III, including the TGF-β. superfamily (BMP-1 through 12, GDF 1 through 12, dpp, 60A, BIP, OF).

Optionally, the growth material may comprise additional osteoconductive bone adhesives, calcium carbonate, fatty acids, lubricants, antiseptic chemicals and/or antibiotics. In this case, other solution excipients such as buffer salts, sugars, anti-oxidants and preservatives to maintain the bioactivity of the growth material and a proper pH of the growth material may be also employed. The additional lubricants and/or the antiseptic and/or the antibiotic will typically be present in the growth material in a predetermined concentration range, which will be dependent upon the particular bone site and application, as well as the specific activity of the antiseptic and/or the antibiotic.

The above description and drawings illustrate preferred embodiments which achieve the objects, features and advantages of the present invention. It is not intended that the present invention be limited to the illustrated embodiments, but rather only by the appended claims.

What is claimed as new and desired to be protected by Letters Patent of the United States is:

1. A method of tissue fixation, comprising:
  securing a first portion of a suture to a tissue to be fixated; and
  anchoring a second portion of the suture into a bone socket using a swivel implant, a separate cannulated fixation device having a threaded body, and a swivel connection between the threaded body and the swivel implant, the swivel implant being attached onto a tip of a driver assembly, the driver assembly comprising a cannulated driver with a shaft, an inserter handle and a tube that passes slidably and rotatably through the cannulated driver, the tube having a tip that accepts the swivel implant, the swivel implant being engaged with the tip of the tube, the tube further having an outer surface for receiving the cannulated fixation device, the driver assembly being pre-loaded with the cannulated fixation device, the swivel implant swivels relative to the cannulated fixation device, the swivel implant comprising a tip and an anchor body, wherein the tip of the swivel implant is configured to capture the suture attached to the tissue, wherein the suture is anchored into the bone socket by the steps of:

capturing the suture attached to the tissue with the swivel implant;
inserting the swivel implant with the captured suture into the bone socket; and
advancing the cannulated fixation device using the driver assembly into the bone socket so that the cannulated fixation device engages the bone socket without excessive twisting of the suture, thereby securing the suture and providing tissue fixation without tying any knots in the suture.

2. The method as recited in claim 1, wherein the suture comprises a plurality of suture loops and the swivel implant comprises a forked tip for capturing the suture.

* * * * *